(12) United States Patent
Peng et al.

(10) Patent No.: US 11,779,462 B2
(45) Date of Patent: Oct. 10, 2023

(54) CONVEYOR AND CONVEYOR SYSTEM

(71) Applicant: Lifetech Scientific (Shenzhen) Co., Ltd., Shenzhen (CN)

(72) Inventors: Feng Peng, Shenzhen (CN); Wei Jiang, Shenzhen (CN); Huixiong Xie, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 145 days.

(21) Appl. No.: 17/418,677

(22) PCT Filed: Oct. 31, 2019

(86) PCT No.: PCT/CN2019/114682
§ 371 (c)(1),
(2) Date: Jun. 25, 2021

(87) PCT Pub. No.: WO2020/134539
PCT Pub. Date: Jul. 2, 2020

(65) Prior Publication Data
US 2022/0061988 A1    Mar. 3, 2022

(30) Foreign Application Priority Data

Dec. 29, 2018  (CN) .......................... 201811646805.8

(51) Int. Cl.
*A61F 2/24*      (2006.01)
*A61M 25/00*   (2006.01)

(52) U.S. Cl.
CPC ... *A61F 2/2436* (2013.01); *A61M 2025/0006* (2013.01)

(58) Field of Classification Search
None
See application file for complete search history.

(56) References Cited

U.S. PATENT DOCUMENTS

2007/0168014 A1   7/2007  Jimenez
2008/0091257 A1   4/2008  Andreas
(Continued)

FOREIGN PATENT DOCUMENTS

CN      204562476 U     8/2015
CN      107080608 A     8/2017
(Continued)

OTHER PUBLICATIONS

First Office Action dated Jan. 6, 2020 in China Appl. No. 201811646805.8, and Translation.
(Continued)

*Primary Examiner* — Shaun L David
(74) *Attorney, Agent, or Firm* — Raymond Sun

(57) ABSTRACT

A conveyor and a conveyor system are provided. The conveyor comprises a lumen assembly and a self-locking mechanism connected to the lumen assembly, wherein the lumen assembly comprises an inner core tube, a recovery sheath movably surrounding the inner core tube, and an outer sheath movably surrounding the recovery sheath; the self-locking mechanism is connected to the recovery sheath; and the outer sheath can move relative to the inner core tube in an axial direction of the conveyor. The self-locking mechanism has a self-locked state and an unlocked state, wherein when the self-locking mechanism is in the unlocked state, the recovery sheath can move relative to the inner core tube in the axial direction of the conveyor; and when the self-locking mechanism is in the self-locked state, the recovery sheath maintains stationary relative to the inner core tube.

10 Claims, 12 Drawing Sheets

(56) References Cited

U.S. PATENT DOCUMENTS

| | | | | |
|---|---|---|---|---|
| 2009/0281619 | A1* | 11/2009 | Le | A61M 25/0147 623/2.11 |
| 2011/0251683 | A1 | 10/2011 | Tabor | |
| 2012/0022629 | A1* | 1/2012 | Perera | C08L 63/00 623/1.11 |
| 2012/0053681 | A1* | 3/2012 | Alkhatib | A61F 2/2418 623/2.11 |
| 2012/0123528 | A1* | 5/2012 | Knippel | A61F 2/2436 623/2.11 |
| 2013/0297011 | A1* | 11/2013 | Morris | A61F 2/2436 623/2.11 |
| 2013/0297012 | A1* | 11/2013 | Willard | A61F 2/2427 623/2.11 |
| 2013/0325115 | A1* | 12/2013 | Maisano | A61B 17/00234 623/2.17 |
| 2014/0277340 | A1* | 9/2014 | White | A61F 2/954 623/1.11 |
| 2016/0000561 | A1* | 1/2016 | Chalekian | A61F 2/2427 623/2.11 |
| 2016/0135975 | A1 | 5/2016 | Shimoyama | |
| 2018/0110622 | A1* | 4/2018 | Gregg | A61F 2/9517 |
| 2018/0147076 | A1 | 5/2018 | Cummins | |
| 2018/0318117 | A1 | 11/2018 | Cummins et al. | |
| 2019/0269510 | A1 | 9/2019 | Zeng et al. | |

FOREIGN PATENT DOCUMENTS

| | | |
|---|---|---|
| CN | 206499552 U | 9/2017 |
| CN | 107550602 A | 1/2018 |
| CN | 108236533 A | 7/2018 |
| CN | 109700575 A | 5/2019 |

OTHER PUBLICATIONS

Response to First Office Action dated Jan. 6, 2020 in China Appl. No. 201811646805.8, and Translation.
Second Office Action dated Sep. 30, 2020 in China Appl. No. 201811646805.8, and Translation.
Response to Second Office Action dated Sep. 30, 2020 in China Appl. No. 201811646805.8, and Translation.
Third Office Action dated Mar. 30, 2021 in China Appl. No. 201811646805.8, and Translation.
Response to Office Action dated Mar. 30, 2021 in China Appl. No. 201811646805.8, and Translation.
Request for Reexamination in China Appl. No. 201811646805.8, and Translation.
Notice of Acceptance of Reexamination Report dated Oct. 11, 2021 in China Appl. No. 201811646805.8, and Translation.
Notice of Reexamination Decision dated Oct. 20, 2021 in China Appl. No. 201811646805.8, and Translation.
First Office Action for corresponding China Application No. 201811646805.8.
Second Office Action for corresponding China Application No. 201811646805.8.
Third Office Action for corresponding China Application No. 201811646805.8.
International Search Report dated Jan. 31, 2020 for corresponding PCT Application No. PCT/CN2019/114682.
European Search Report dated Jan. 28, 2022 for corresponding European Application No. EP 19 90 2554.
Office Action dated Feb. 25, 2022 for corresponding India Application No. 202127030599.
Notice of Grant dated Nov. 22, 2021 for corresponding China Application No. 201811646805.8 and Translation thereof.
Response to first office action for corresponding China Application No. 201811646805.8 and translation thereof.
Response to second office action for corresponding China Application No. 201811646805.8 and translation thereof.
Response to third office action for corresponding China Application No. 201811646805.8 and translation thereof.
Claims submitted with Response to third office and allowed in Notice of Grant dated Nov. 22, 2021 for corresponding China Application No. 201811646805.8.
Translation of Claims submitted with Response to third office and allowed in Notice of Grant dated Nov. 22, 2021 for corresponding China Application No. 201811646805.8.

\* cited by examiner

CONVEYOR AND CONVEYOR SYSTEM

FIELD OF THE INVENTION

The disclosure relates to the technical field of medical apparatuses, and in particular, relates to a conveyor and a conveyor system.

BACKGROUND

The human heart includes four valves (mitral valve, aortic valve, pulmonary valve and tricuspid valve) which ensure that blood delivered by the heart flows in the cardiovascular system according to a specified direction. The mitral valve is located between the left atrium and the left ventricle. A healthy mitral valve can ensure that the blood flows from the left atrium to the left ventricle. When the left ventricle shrinks, two flexible lobules of the mitral valve are closed to prevent the blood from flowing back from the left ventricle to the left atrium. Lesions on each mitral valve may cause dysfunction of the mitral valve organ, causing the mitral valve to become abnormally constricted to allow the blood to flow back from the left ventricle into the left atrium, thereby affecting the normal work of the heart and the life of the patient In view of the mitral valve dysfunction, there are many methods to treat mitral valve dysfunction. The conventional valve replacement operation is known as a "open heart" surgery. In short, during the surgery, the chest is opened surgically, extracorporeal circulation is initiated with a heart-lung machine, the heart is stopped and opened, and then the mitral valve of a patient is removed and replaced. However, due to the complicated operation of the extracorporeal circulation and poor tolerability of elderly patients, there is often a high risk of death. In addition, since interventional treatment for the mitral valve is less invasive to a patient, this therapy is increasingly preferred. In such techniques, a self-expanding valve prosthesis is typically installed at an end of a flexible catheter in a crimped state and pushed along a blood vessel of a patient until the valve prosthesis reaches an implantation site. The valve prosthesis then expands to its normal size at the site of a defective native mitral valve.

Although this therapy creates little trauma to the patient during treatment, due to a higher radial supporting force of a valve stent of the valve prosthesis, it can be difficult to load the valve prosthesis into a conveying catheter prior to surgery. It will also be appreciated that it can be difficult to release the valve prosthesis loaded into the conveying catheter from the conveying catheter during the operation process due to the higher radial supporting force of the valve prosthesis. In addition, during the process of loading or releasing of the valve prosthesis, since the supporting force of the valve stent of the valve prosthesis is too high, the conveying catheter can be easily deformed, such that the operation cannot be successfully completed.

SUMMARY

Based on the above, there is a need to provide a conveyor to solve the problem in the prior art, that it can be difficult to load a valve prosthesis into a conveying catheter.

A conveyor includes a lumen assembly and a self-locking mechanism connected to the lumen assembly. The lumen assembly includes an inner core tube, a recovery sheath movably surrounding the inner core tube, and an outer sheath movably surrounding the recovery sheath. The self-locking mechanism is connected to the recovery sheath; the outer sheath can move relative to the inner core tube in an axial direction of the conveyor; the self-locking mechanism has a self-locked state and an unlocked state, wherein when the self-locking mechanism is in the unlocked state, the recovery sheath can move relative to the inner core tube in the axial direction of the conveyor; and when the self-locking mechanism is in the self-locked state, the recovery sheath maintains stationary relative to the inner core tube.

In one of the embodiments, the conveyor further includes a housing assembly; an accommodating slot is formed in the housing assembly; the lumen assembly and the self-locking mechanism are mounted in the accommodating slot; a rack track is formed on an inner side wall of the housing assembly; the self-locking mechanism includes a limiting member connected to the recovery sheath; the limiting member includes a main body and limiting teeth formed on the main body; the limiting teeth cooperate with the rack track; the limiting member movably cooperates with the recovery sheath in a radial direction of the recovery sheath, wherein when the limiting teeth follow the limiting member to move in the radial direction of the recovery sheath to mesh with the rack track, the self-locking mechanism is switched to the self-locked state; and after the limiting teeth follow the limiting member to move in the radial direction of the recovery sheath to be separated from the rack track, the self-locking mechanism is switched to the unlocked state.

In one of the embodiments, the recovery sheath includes a recovery sheath body and a sheath joint fixed at a proximal end of the recovery sheath body, and a groove or a bulge is arranged on the sheath joint, wherein when a groove is formed in the sheath joint, a bulge aligned with the groove is formed on the main body; when a bulge is arranged on the sheath joint, a groove aligned with the bulge is formed in the main body; the bulge movably cooperates with the groove; and the limiting member movably cooperates with the recovery sheath through the bulge.

In one of the embodiments, a tooth height of the rack track is equal to a tooth height of the limiting teeth; a protruding length of the bulge is greater than or equal to the tooth height of the rack track; and a depth of the groove is greater than or equal to the tooth height of the rack track.

In one of the embodiments, the recovery sheath further includes a necking structure; the necking structure is fixed at a distal end of the recovery sheath body; an inner diameter of the necking structure is gradually reduced in a direction from the distal end to the proximal end; an inner diameter of the proximal end of the necking structure is equal to an inner diameter of the distal end of the recovery sheath body; and the maximum outer diameter of the necking structure is less than or equal to an inner diameter of the outer sheath.

In one of the embodiments, a central axis of the recovery sheath is aligned with a central axis of the housing assembly; two rack tracks are provided; the two rack tracks are symmetrically distributed in a diameter direction of the recovery sheath; two limiting members are provided; the limiting members are in one-to-one correspondence with the rack tracks; the self-locking mechanism further comprises elastic members compressed between the two limiting members; a force application direction of an elastic force generated by the elastic members is perpendicular to the central axis of the housing assembly; and the elastic force generated by the elastic members drives the limiting teeth of the two limiting members to move to mesh with the rack tracks.

In one of the embodiments, the elastic members are arranged in pairs; the paired elastic members are respectively located on two sides of the recovery sheath; and two adjacent pairs of elastic members are arranged to extend along an axial line of the recovery sheath.

In one of the embodiments, a track hole extending in an axial direction of the housing assembly is also formed in the housing assembly; the track hole and the accommodating slot extend through each other; an extending direction of the track hole is the same as an extending direction of the rack track; the track hole is formed in the rack track; the limiting member further comprises a connection portion fixedly connected to the main body; the connection portion extends out of the track hole from the accommodating slot; and the connection portion movably cooperates with the track hole.

In one of the embodiments, the limiting member further includes a button, and the button is fixedly connected to the connection portion.

One embodiment further provides a conveyor system, including a valve prosthesis and the above-mentioned conveyor, and the valve prosthesis is detachably connected to the lumen assembly of the conveyor.

The above-mentioned conveyor is used for conveying the valve prosthesis; a distal end of the inner core tube is connected with a valve stent of the valve prosthesis to switch the self-locking mechanism to the unlocked state; the recovery sheath can slide in its axial direction to cause a partial structure at a proximal end of a bare stent to be accommodated into an inner cavity of the recovery sheath; the recovery sheath compresses the valve stent to reduce a radial size of the valve stent, and the self-locking mechanism is then switched to the self-locked state, so that the recovery sheath maintains stationary relative to the inner core tube (that is, the recovery sheath cannot slide in its axial direction), and the recovery sheath continues compressing the valve stent, which can reduce the resistance to the conveyor for loading or releasing the valve prosthesis, and then make it less difficult for the conveyor to load or release the valve prosthesis.

DETAILED DESCRIPTION OF THE EMBODIMENTS

In order to make the above objectives, features and advantages of the present invention more easily understandable, specific implementation modes of the present invention are described in detail below in conjunction with the accompanying drawings. Many specific details are explained in the following descriptions to facilitate fully understanding the present invention. However, the present invention may be embodied in many different forms from those herein set forth, and those skilled in the art can make similar modifications without departing from the concept of the present invention, so that the present invention is not limited by the specific implementations disclosed below.

It should be noted that when an element is referred to as being "fixed" or "arranged" to another element, it can be directly on another element or an intermediate element may also exist. When an element is referred to as being "connected" to another element, it can be directly connected to another element or an intermediate element may also exist. The terms "vertical", "horizontal", "left", "right" and similar expressions used herein are only for the purpose of explanation, and do not denote the unique implementation mode.

Unless defined otherwise, all technical and scientific terms used herein have the same meaning as commonly understood by those of ordinary skill in the art to which the present invention belongs. The terms used in the description of the present invention is for the purpose of describing specific implementation modes only and are not intended to limiting the present invention. As used herein, the term "and/or" includes any and all combinations of one or more of the associated listed items.

To more clearly describe the structures of the present application, "distal end" and "proximal end" are used as localizers, wherein "distal end" refers to an end away from an operator in a surgical process, and "proximal end" refers to an end close to the operator in the surgical process.

Figure 1:
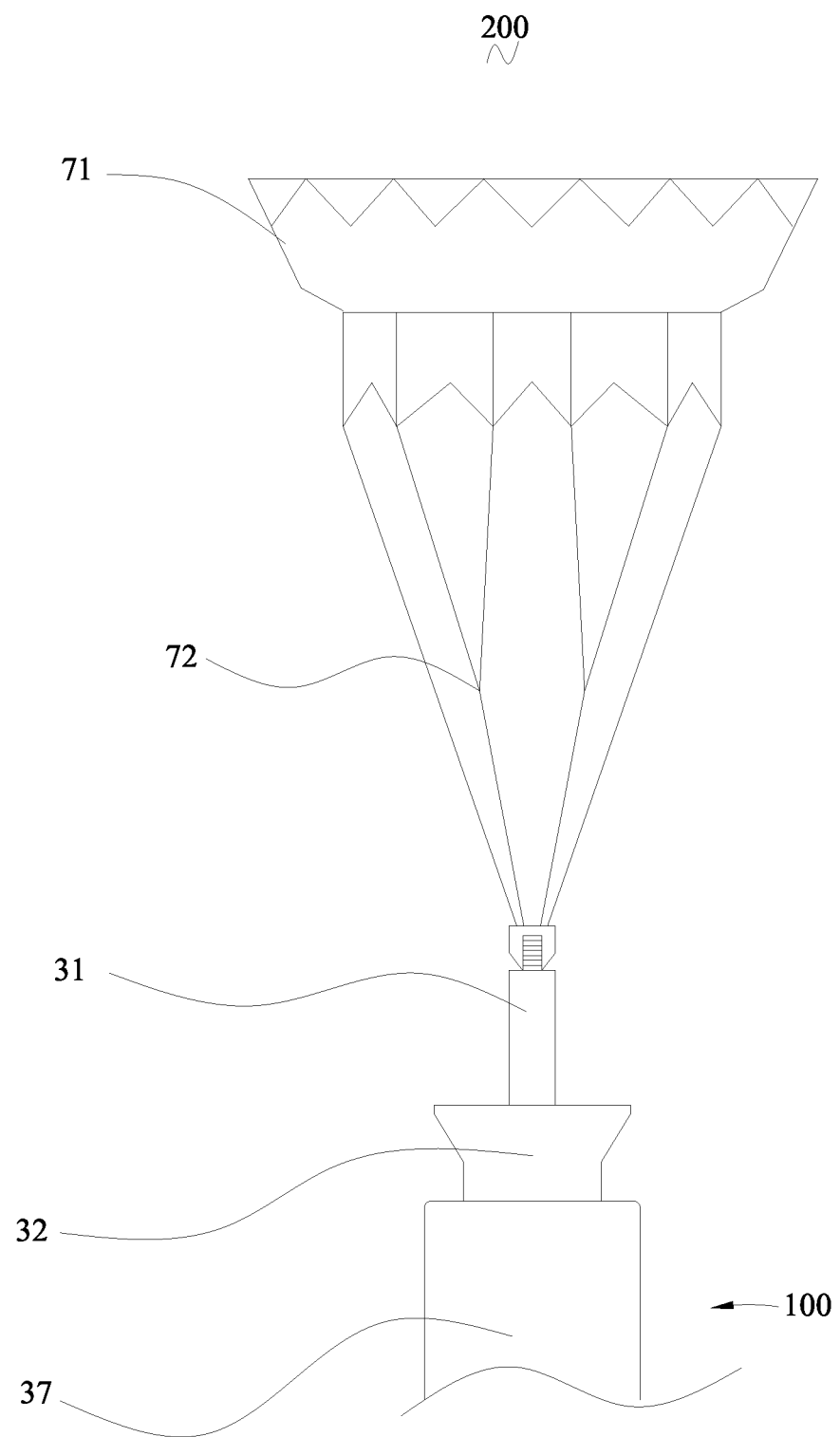
FIG. 1 is a diagram of a first state of cooperation between a conveyor and a valve prosthesis according to one embodiment.

As shown in FIG. 1, a conveyor 100 provided by one embodiment is used for conveying a valve prosthesis 71. The valve prosthesis 71 includes a valve stent 72, and the valve stent 72 may generate a radial extension force.

Figure 2:
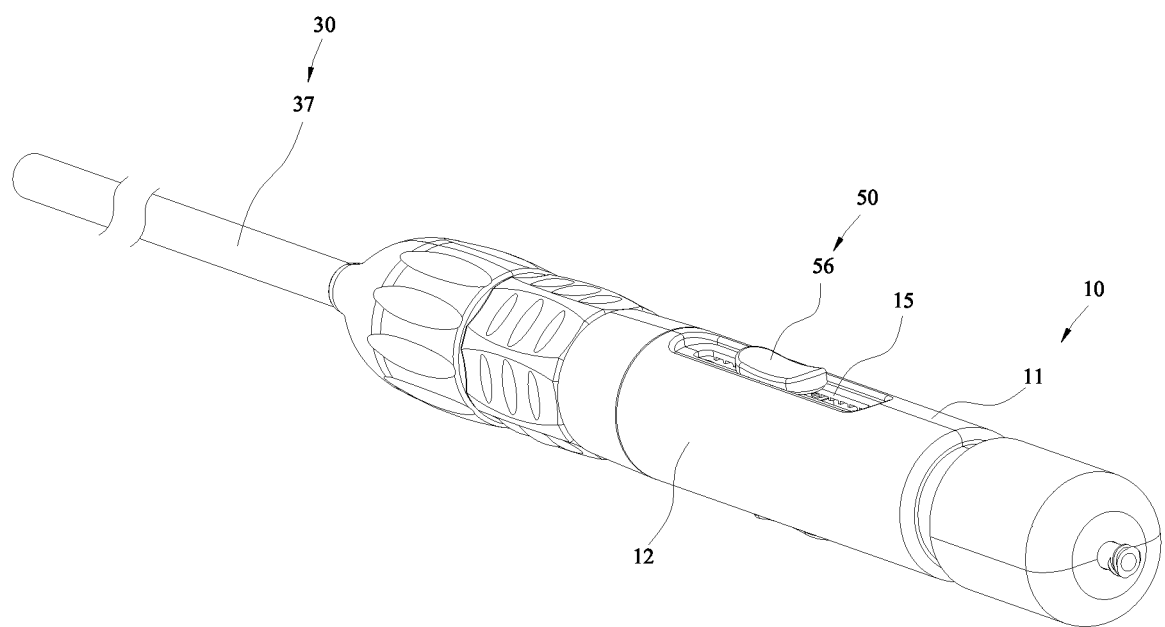
FIG. 2 is a three-dimensional diagram of a conveyor according to one embodiment.
Figure 3:
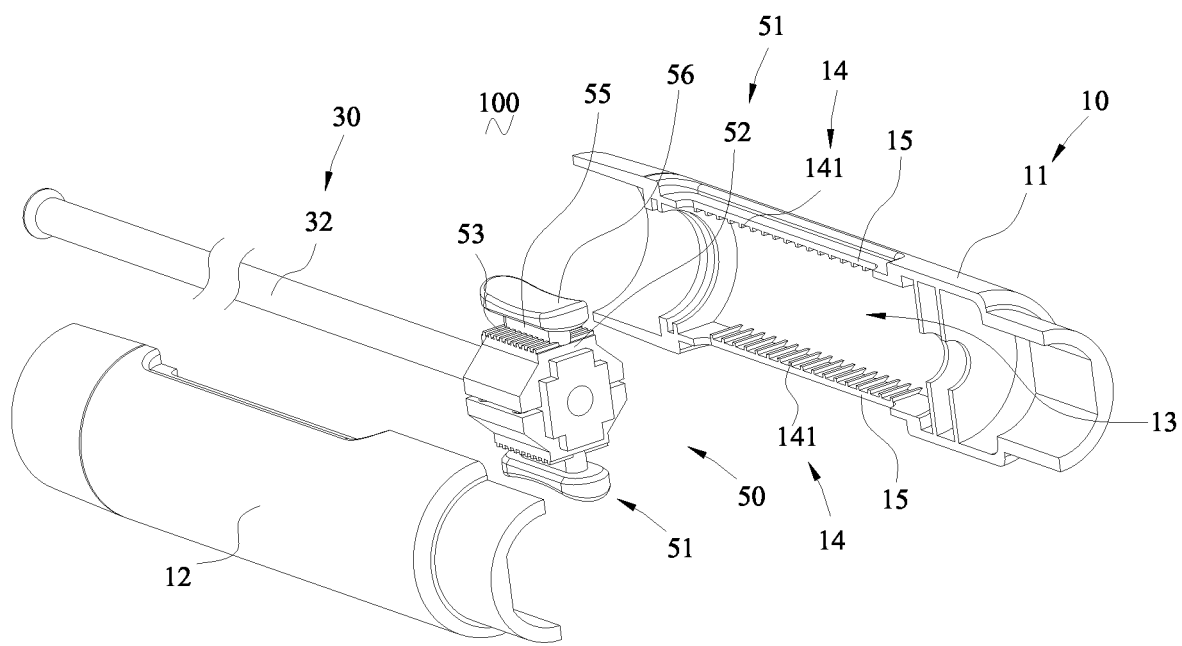
FIG. 3 is a three-dimensional exploded diagram of a partial structure of a conveyor according to one embodiment.

As shown in FIG. 2 and FIG. 3, the conveyor 100 includes a housing assembly 10, a lumen assembly 30 and a self-locking mechanism 50. The lumen assembly 30 is connected to the self-locking mechanism 50; an accommodating slot 13 is defined in the housing assembly 10; and both the lumen assembly 30 and the self-locking mechanism 50 are mounted in the accommodating slot 13.

The housing assembly 10 has a central axis. As shown in FIG. 2, the housing assembly 10 includes a male housing 11 and a female housing 12. Both the male housing 11 and the female housing 12 extend along the central axis of the housing assembly 10; an interface is defined at a boundary between the female housing 12 and the male housing 11; and the central axis of the housing assembly 10 is located in the interface.

The male housing 11 and the female housing 12 are mutually buckled and define the accommodating slot 13; an opening of the accommodating slot 13 faces a distal end of the housing assembly 10, and the central axis of the housing assembly 10 coincides with a geometric central line of the accommodating slot 13.

A rack track 14 is formed on an inner side wall of the housing assembly 10, and the rack track 14 includes a number of teeth-shaped members 141. The rack track 14 extends in a direction of the central axis of the housing assembly 10. In one embodiment, there are two rack tracks 14, and the two rack tracks 14 are symmetrically distributed about the central axis of the housing assembly 10. Either rack track 14 is divided into two equal halves by the interface (i.e., one half of either rack track 14 is located on the male housing 11, and the other half is located on the female housing 12).

As shown in FIG. 2 and FIG. 3, two track holes 15, which are communicated with the accommodating slot 13, are defined in the housing assembly 10; the track holes 15 are in one-to-one correspondence with the rack tracks 14; and the track holes 15 are defined in the corresponding rack tracks 14. An extending direction of the rack tracks 14 is the same as an extending direction of the track holes 15. Either track hole 15 is divided into two equal halves by the interface (i.e. one half of either track hole 15 is located on the male housing 11 and the other half is located on the female housing 12). The track holes 15 extend along the central axis of the housing assembly 10.

Figure 4:
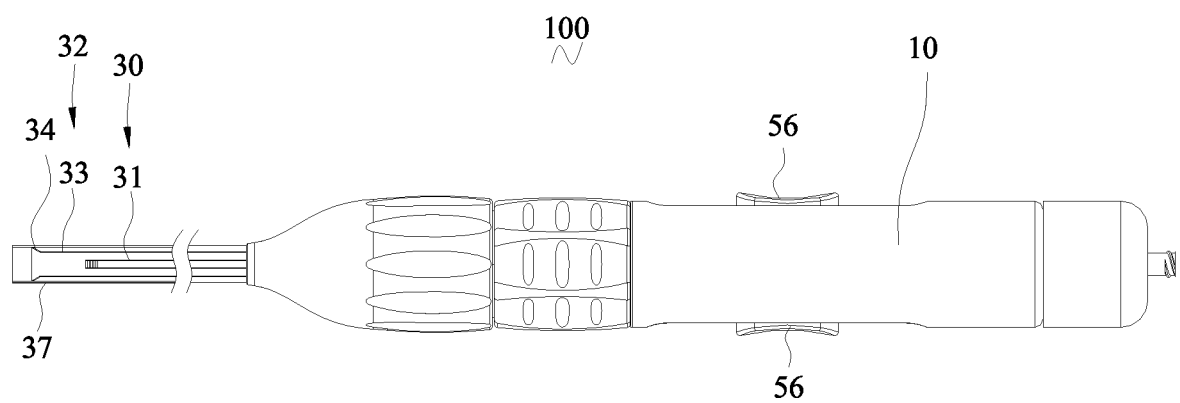
FIG. 4 is a schematic structural diagram of a conveyor according to one embodiment.

As shown in FIG. 4, the lumen assembly 30 includes an inner core tube 31, a recovery sheath 32 and an outer sheath 37 which are coaxially mounted, and the inner core tube 31, the recovery sheath 32 and the outer sheath 37 are all mounted in the accommodating slot 13. Specifically, proximal ends of the inner core tube 31, the recovery sheath 32 and the outer sheath 37 are all accommodated in a slot cavity of the accommodating slot 13, and distal ends of the inner core tube 31, the recovery sheath 32 and the outer sheath 37 all extend out of the accommodating slot 13 from the opening of the accommodating slot 13, so that the distal end of the inner core tube 31 is connected to a proximal end of the valve stent 72 beyond the accommodating slot 13, and an operator can operate the valve stent 72 conveniently.

A central axis of the recovery sheath 32 coincides with the central axis of the housing assembly 10. The recovery sheath 32 movably surrounds the inner core tube 31. The recovery sheath 32 may axially slide back and forth along its central axis relative to the inner core tube 31; when the recovery sheath 32 slides in a direction from its proximal end to its distal end, the distal end of the recovery sheath 32 may radially compress the valve stent 72 of the valve prosthesis 71, so that a radial size of the valve stent 72 may be compressed, and a partial structure of a proximal end of the valve stent 72 is received into an inner cavity of the recovery sheath 32. The outer sheath 37 movably surrounds the recovery sheath 32, and the outer sheath 37 may axially slide back and forth along its central axis relative to the inner core tube 31 and the recovery sheath 32. When the outer sheath 37 slides in a direction from its proximal end to its distal end, the distal end of the outer sheath 37 may radially compress the valve stent 72 of the valve prosthesis 71, and the valve prosthesis 71 is received into an inner cavity of the outer sheath 37.

During use, the recovery sheath 32 first slides in the direction from its proximal end to its distal end to cause the distal end of the recovery sheath 32 to compress the valve stent 72. Then the outer sheath 37 slides in the direction from its proximal end to its distal end to cause the valve prosthesis 71 to be received into the outer sheath 37. During this process, the radial size of the valve stent 72 compressed by the recovery sheath 32 will be reduced, so that a radial force generated by the valve stent 72 to a side wall of the outer sheath 37 will be greatly reduced, and then a frictional resistance between the outer sheath 37 and the stent of the valve prosthesis 71 is reduced, thereby reducing a counter-acting force applied by the valve stent 72 to the outer sheath 37 (the counter-reacting force drives the outer sheath 37 to slide in a direction from its distal end to its proximal end), which may in turn reduce the difficulty of loading the valve prosthesis 71 into the inner cavity of the outer sheath 37. At the same time, when the valve prosthesis 71 is received into the inner cavity of the outer sheath 37, deformation of the outer sheath 37 caused by the counter-reacting force of the valve prosthesis 71 to the outer sheath 37 and destructive deformation of the valve stent 72 caused by excessive frictional resistance between the outer sheath 37 and the valve prosthesis 71 can also be avoided.

The recovery sheath 32 includes a recovery sheath body 33, a necking structure 34 and a sheath joint 35. The recovery sheath body 33 is a straight tubular structure, and the recovery sheath body 33 defines the inner cavity of the recovery sheath 32. The recovery sheath body 33 may receive the partial structure of the proximal end of the valve stent 72, and has its distal end that radially compresses the proximal end of the valve stent 72.

Figure 5:
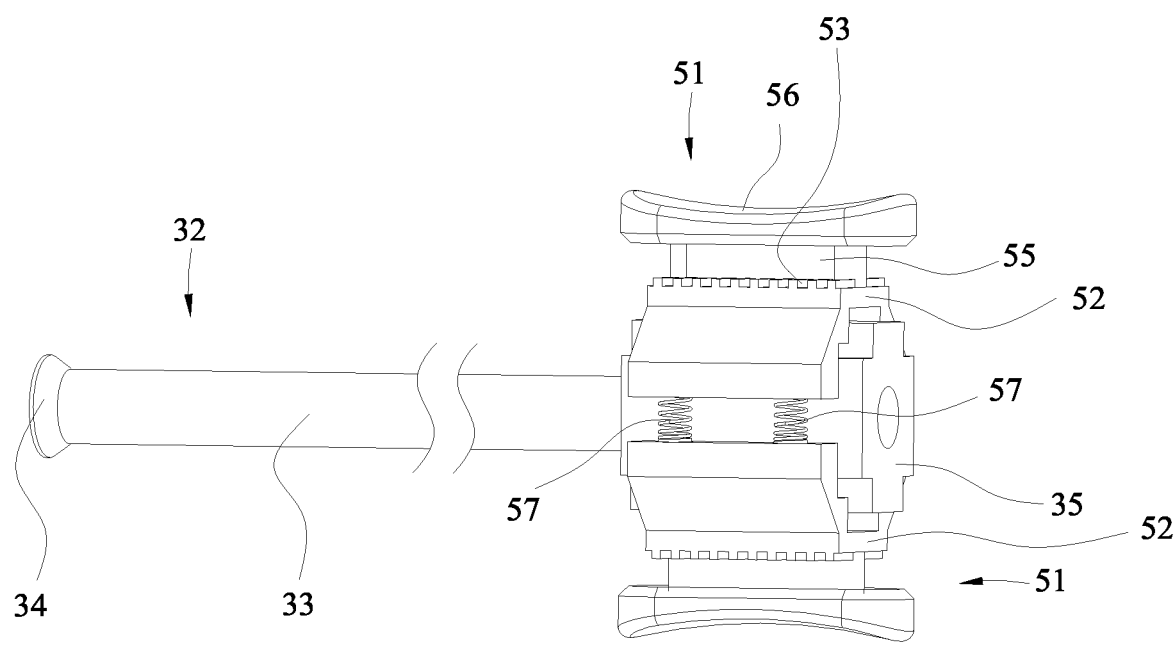
FIG. 5 is a three-dimensional diagram of a recovery sheath and a self-locking mechanism according to one embodiment.

As shown in FIG. 5, the necking structure 34 is fixed to a distal end of the recovery sheath body 33. The necking structure 34 has a horn shape; and an inner diameter of the necking structure 34 is gradually reduced in a direction from its distal end to its proximal end. When the recovery sheath 32 receives the proximal end of the valve stent 72 into its inner cavity, the proximal end of the valve stent 72 may conveniently enter the inner cavity of the recovery sheath 32. An inner diameter of the proximal end of the necking structure 34 is equal to an inner diameter of the distal end of the recovery sheath body 33, so that an inner wall of the recovery sheath 32 remains smooth at all times, thereby allowing the valve stent 72 to be received the recovery sheath 32 . The maximum outer diameter of the necking structure 34 is less than or equal to an inner diameter of the outer sheath 37, so that interference between the necking structure 34 and the outer sheath 37 can be avoided to ensure that the outer sheath 37 can slide back and forth in its axial direction relative to the recovery sheath 32 to cause the valve prosthesis 71 to be received into the inner cavity of the outer sheath 37 and release the valve prosthesis 71 from its inner cavity.

Figure 6:
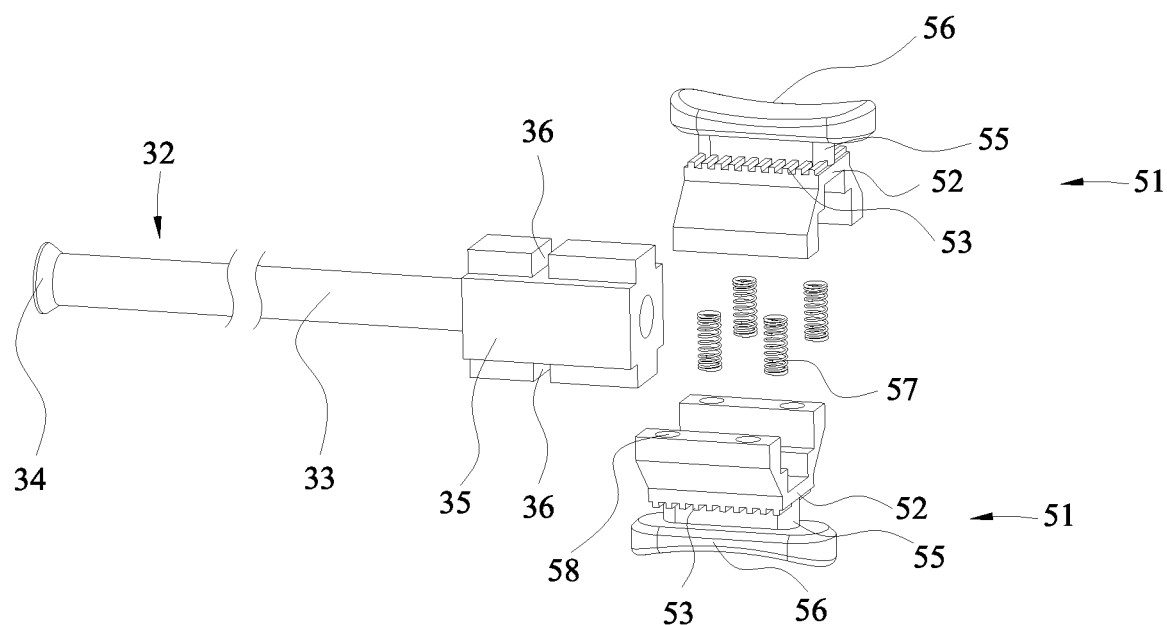
FIG. 6 is a three-dimensional exploded diagram of a recovery sheath and a self-locking mechanism according to one embodiment.

The sheath joint 35 is fixed to a proximal end of the recovery sheath body 33. Specifically, the sheath joint 35 may be fixed with the recovery sheath body 33 to form an integrated structure via gluing, buried injection molding, or other connection techniques. As shown in FIG. 6, the sheath joint 35 is accommodated in the accommodating slot 13. The sheath joint 35 is provided with a groove 36. The self-locking mechanism 50 is connected to the recovery sheath 32. The self-locking mechanism 50 has a self-locked state and an unlocked state. When the self-locking mechanism 50 is in the unlocked state, the recovery sheath 32 may slide axially along its central axis relative to the inner core tube 31; and when the self-locking mechanism 50 is in the self-locked state, the recovery sheath 32 remains stationary relative to the inner core tube 31. It should be noted that "stationary" means that the recovery sheath 32 cannot slide in its axial direction relative to the inner core tube 31.

When the recovery sheath 32 slides in the direction from its proximal end to its distal end to cause the partial structure of the proximal end of the valve stent 72 to be received into the inner cavity of the recovery sheath 32, the valve stent 72 would generate a relatively high radial extension force, and the valve stent 72 exposed from the inner cavity of the recovery sheath 32 generates a counter-reacting force to the recovery sheath 32. The counter-reacting force may drive the outer sheath 37 to slide in the direction from its distal end to its proximal end, i.e., it may drive the recovery sheath 32 to release the valve stent 72 in its inner cavity.

The self-locking mechanism 50 is switched to the self-locked state, and the recovery sheath 32 remains stationary relative to the inner core tube 31, so as to ensure that the valve stent 72 received into the inner cavity of the recovery sheath 32 cannot be withdrawn in a reverse direction, so as to cause the recovery sheath 32 to continue compressing the valve stent 72, thereby ensuring that the counter-reacting force generates minimal influence on the outer sheath 37 in the whole process that the outer sheath 37 receives the valve prosthesis 71 into its inner cavity, thereby making it easier to load, via the outer sheath 37, the valve prosthesis 71, and improving the convenience of loading, via the conveyor 100, the valve prosthesis 71. Moreover, when loading the valve prosthesis 71 via the conveyor 100, an operator does not need to manually brake the recovery sheath 32 under the self-locking action of the self-locking mechanism 50, so that a labor-saving effect can be achieved. It can be understood that the self-locking mechanism 50 acts during recovery of the valve prosthesis 71, as does the self-locking mechanism 50 during loading of the valve prosthesis 71.

When the self-locking mechanism 50 is in the unlocked state, the recovery sheath 32 slides axially back and forth along its central axis relative to the inner core tube 31. This allows the recovery sheath 32 to receive the proximal end of the valve stent 72 into the inner cavity of the recovery sheath 32, and allows the recovery sheath 32 to release the valve stent 72 from its inner cavity.

As shown in FIG. 5 and FIG. 6, in one embodiment, the self-locking mechanism 50 includes two limiting members 51 connected to the recovery sheath 32, and elastic members 57 compressed between the two limiting members 51. The limiting members 51 may be in limited cooperation with the housing assembly 10. The self-locking mechanism 50 is in the self-locked state when the limiting members 51 are in limited cooperation with the housing assembly 10. The self-locking mechanism 50 is in the unlocked state when the limiting members 51 are in other cooperational relationships with the housing assembly 10 (for example, the limiting members 51 are in non-limited cooperation with the housing assembly 10).

The two limiting members 51 are symmetrically distributed in a radial direction of the recovery sheath 32, and are opposite to each other. The limiting members 51 are in one-to-one correspondence with the rack tracks 14. Each limiting member 51 includes a main body 52 and limiting teeth 53 arranged on the main body 52. The limiting teeth 53 cooperate with the corresponding rack track 14. When the limiting teeth 53 mesh with the rack tracks 14, the limiting members 51 remain stationary in their axial directions relative to the inner core tube 31 and a housing to cause the self-locking mechanism 50 to be in the self-locked state.

Figure 7:
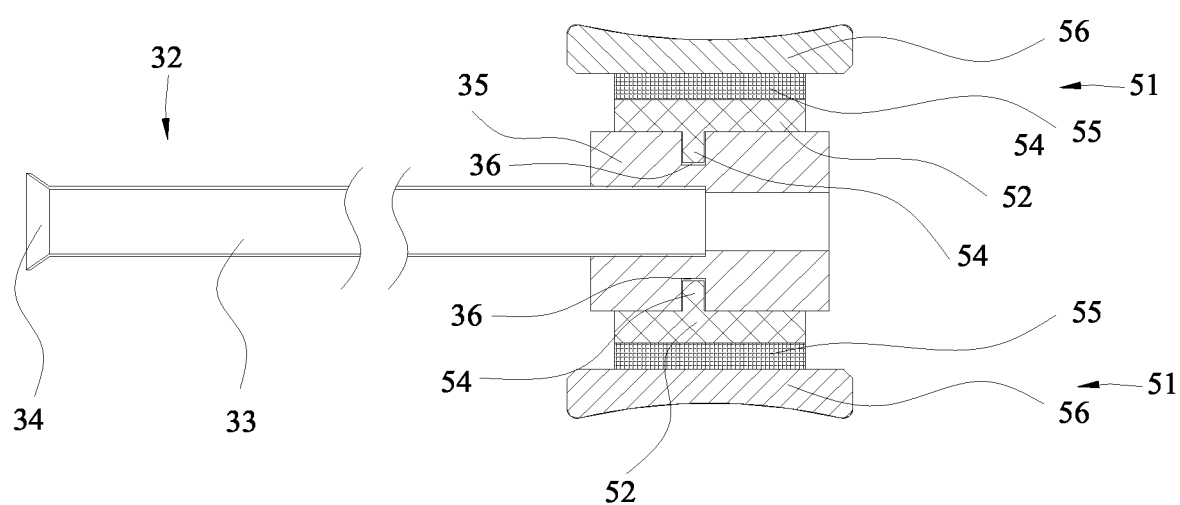
FIG. 7 is a schematic sectional structural diagram of a recovery sheath and a self-locking mechanism according to one embodiment.

The limiting members 51 and the grooves 36 are in one-to-one correspondence with the rack tracks 14, and the limiting member 51 and the groove 36 that correspond to the same rack track 14 correspond to each other. The limiting member 51 is located between the corresponding rack track 14 and groove 36. As shown in FIG. 7, bulges 54 aligned with the grooves 36 are defined on the bodies 52 (that is, the shapes of the bulges 54 are the same as the shapes of openings of the grooves 36, and the sizes of the bulges 54 are identical to the sizes of the grooves 36 to avoid swinging of the bulges 54 during insertion into and withdrawal from the grooves 36), and the bulges 54 face away from the limiting teeth 53. The bulges 54 are in sliding cooperation with the grooves 36. When the limiting members 51 are in the sliding cooperation with the recovery sheath 32 through the bulges 54, the limiting members 51 drive the limiting teeth 53 to slide in the radial direction of the recovery sheath 32 to cause the limiting teeth 53 to mesh with or to be separated from the rack tracks 14, so that the self-locking mechanism 50 can be locked and unlocked by itself.

It can be understood that the conveyor 100 can also realize a self-locking function by cooperation of one limiting piece 51 with one rack track 14, while the present embodiment provides two limiting members 51, which also achieve the same technical effect. Meanwhile, two limiting members 51 can also prevent a mis-operation caused by mis-touch of the limiting members 51 during operation.

When the limiting teeth 53 move to mesh with the rack tracks 14, the limiting members 51 will not move along the center axis of the housing assembly 10 and the central axis of the inner core tube 31, so that the recovery sheath 32 remains stationary relative to the inner core tube 31, and the self-locking mechanism 50 is switched to the self-locked state. When the limiting teeth 53 move to be separated from the rack tracks 14, the limiting members 51 can move along the center axis of the housing assembly 10 and the central axis of the inner core tube 31, so that the limiting members 51 can drive the recovery sheath 32 to move axially relative to the inner core tube 31, and the self-locking mechanism 50 is switched to the unlocked state.

A tooth height of the rack tracks 14 is equal to a tooth height of the limiting teeth 53; a protruding length of the bulges 54 is greater than or equal to the tooth height of the rack tracks 14; and a depth of the grooves 36 is greater than or equal to the tooth height of the rack tracks 14. It can be ensured that the bulges 54 will not slide out from the grooves 36 at all times when the limiting members 51 moves in the radial direction of the recovery sheath 32, thereby ensuring that the self-locking and unlocking operations of the self-locking mechanism 50 can be accomplished.

Of course, in other embodiments, the positions of the bulges 54 and the grooves 36 may be interchanged. Specifically, the bulges 54 can be arranged on the sheath joint 35; the bulges 54 extend in the radial direction of the recovery sheath 32 toward the limiting members 51; and the grooves 36 are formed in the limiting members 51.

As shown in FIG. 6 and FIG. 7, the limiting members 51 further include connection portions 55 and buttons 56. The connection portions 55 are fixedly connected to the bodies 52, and the connection portions 55 extend out of the track holes 15 from the accommodating slot 13; and the connection portions 55 are in sliding cooperation with the track holes 15. When the self-locking mechanism 50 is in the unlocked state, and the connection portions 55 slide in the track holes 15 in the axial direction of the recovery sheath 32, the limiting members 51 drive the recovery sheath 32 to axially slide. When the connection portions 55 slide in the track holes 15 in the radial direction of the recovery sheath 32, the limiting teeth 53 on the bodies 52 may be driven to mesh with or be separated from the rack tracks 14 to cause the self-locking mechanism 50 to be self-locked or unlocked.

The buttons 56 are fixedly connected to the connection portions 55. An acting force may be applied to the connection portions 55 by the buttons 56, and the connection portions 55 drive the limiting members 51 to move in the axial direction or the radial direction.

As shown in FIG. 6, four accommodation holes 58 are also defined in the bodies 52, and the two bodies 52 are arranged to face each other. The accommodation holes 58 in the two bodies 52 are arranged to face each other, and the central axes of two accommodation holes 58 which face each other are aligned.

Each elastic member 57 is loaded into two accommodation holes 58 facing each other. A force application direction of the elastic force generated by two elastic members 57 is perpendicular to the central axis of the housing assembly 10, and the elastic force generated by the elastic members 57 drives the limiting teeth 53 of the two limiting members 51 to move in the radial direction of the recovery sheath 32 to mesh with the rack tracks 14. When the limiting members 51 are subjected to an external force, the external force compresses the limiting members 51 in the radial direction of the recovery sheath 32. The external force is greater than the elastic force generated by the elastic members 57. The limiting members 51 cooperate with the grooves 36 by the bulges 54, so that the limiting members 51 move close to the recovery sheath 32 in the radial direction of the recovery sheath 32, and drive the limiting teeth 53 to be separated from the rack tracks 14, and the self-locking mechanism 50 is switched to the unlocked state. When the self-locking mechanism 50 is in the unlocked state, an axial acting force is applied to the limiting members 51, and the limiting members 51 can drive the recovery sheath 32 to move axially. After the external force is removed, the elastic force of the elastic members 57 drives the limiting members 51 away from the recovery sheath 32 in the radial direction of the recovery sheath 32, and the limiting teeth 53 mesh with the rack tracks 14.

In one embodiment, there are four elastic members 57. The elastic members 57 are arranged in pairs, and the paired elastic members 57 are respectively located on two sides of the recovery sheath 32, and the paired elastic members 57 are symmetric about the interface. When the limiting members 51 slide to mesh with the rack tracks 14, it can be ensured that a stress on the limiting members 51 is balanced in a plane perpendicular to the central axis of the housing assembly 10, thereby guaranteeing the stability of the sliding process. Two adjacent pairs of elastic members 57 are arranged in an extending manner along the axis of the recovery sheath 32. The stress on the limiting members 51 can be ensured to be balanced.

Of course, in other embodiments, there may also be two, six, eight, and other even numbers of elastic members 57.

In one embodiment, a conveyor system 200 is provided, including a valve prosthesis 71 and the above-mentioned conveyor 100. The valve prosthesis 71 is detachably connected to the lumen assembly 30 of the conveyor 100.

Specifically, as shown in FIG. 1, the valve prosthesis 71 includes a valve stent 72. A proximal end of the valve stent 72 is connected to a distal end of the inner core tube 31. The valve stent 72 of the valve prosthesis 71 is connected to the inner core tube 31 to achieve a first state of the conveyor system 200.

Figure 8A:
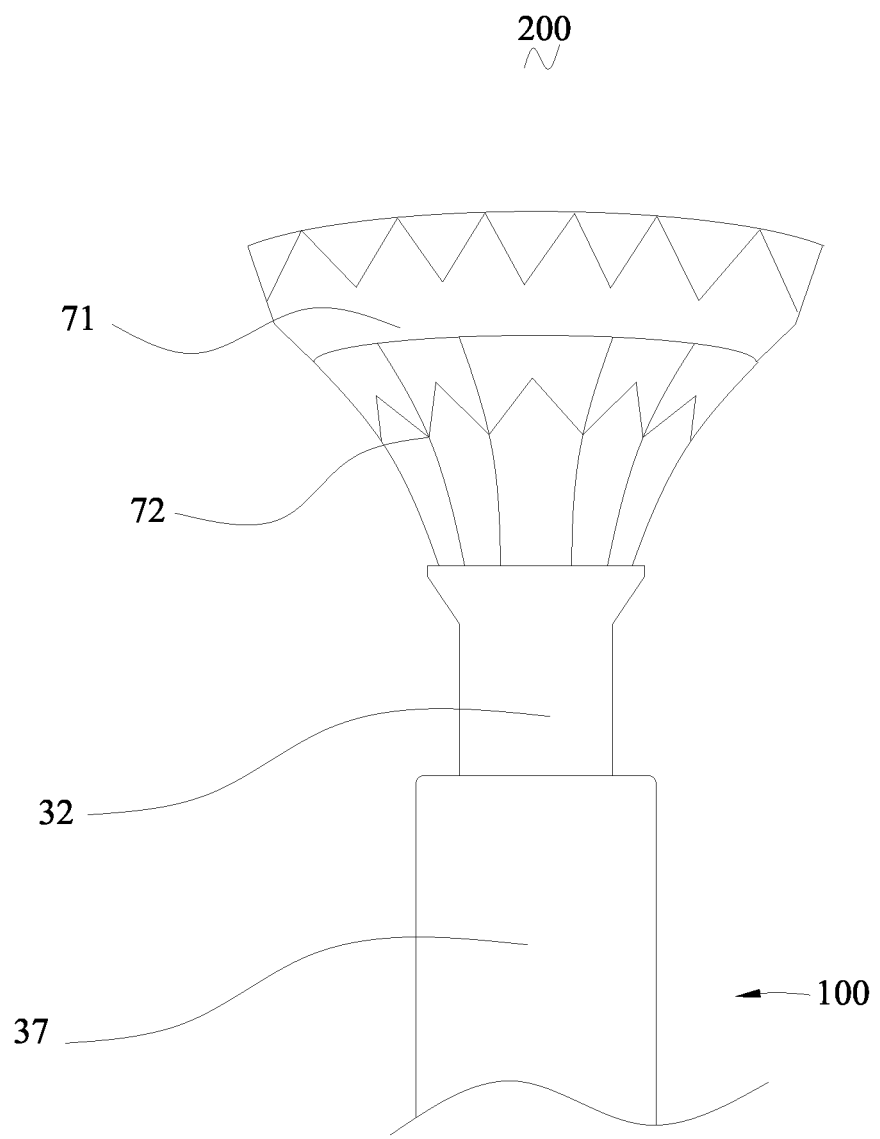
FIG. 8A is a diagram of a second state of cooperation between a conveyor and a valve prosthesis according to one embodiment.

When the valve prosthesis 71 is received into the inner cavity of the outer sheath 37, a radial compression force is simultaneously applied to the two buttons 56 to cause the limiting members 51 to move, in the radial direction of the recovery sheath 32, close to the recovery sheath 32, so that the limiting teeth 53 are separated from the rack tracks 14, and the self-locking mechanism 50 is switched to the unlocked state. As shown in FIG. 8A, the recovery sheath 32 may slide in the direction from its proximal end to its distal end to cause the proximal end of the valve stent 72 to be received into the recovery sheath 32. After the valve stent 72 is surrounded by the proximal end of the recovery sheath 32, the radial size of the proximal end of the valve stent 72 is compressed. The proximal end of the valve stent 72 being received into the inner cavity of the recovery sheath 32 is a second state of the conveyor system 200.

The two buttons 56 are loosened, and the elastic members 57 drive the limiting members 51 to slide in the radial direction of the recovery sheath 32, so that the limiting teeth 53 mesh with the rack tracks 14, and the self-locking mechanism 50 is switched to the self-locked state; the recovery sheath 32 cannot slide in its axial direction, and the recovery sheath 32 maintains a state of radially compressing the valve stent 72.

Figure 8B:
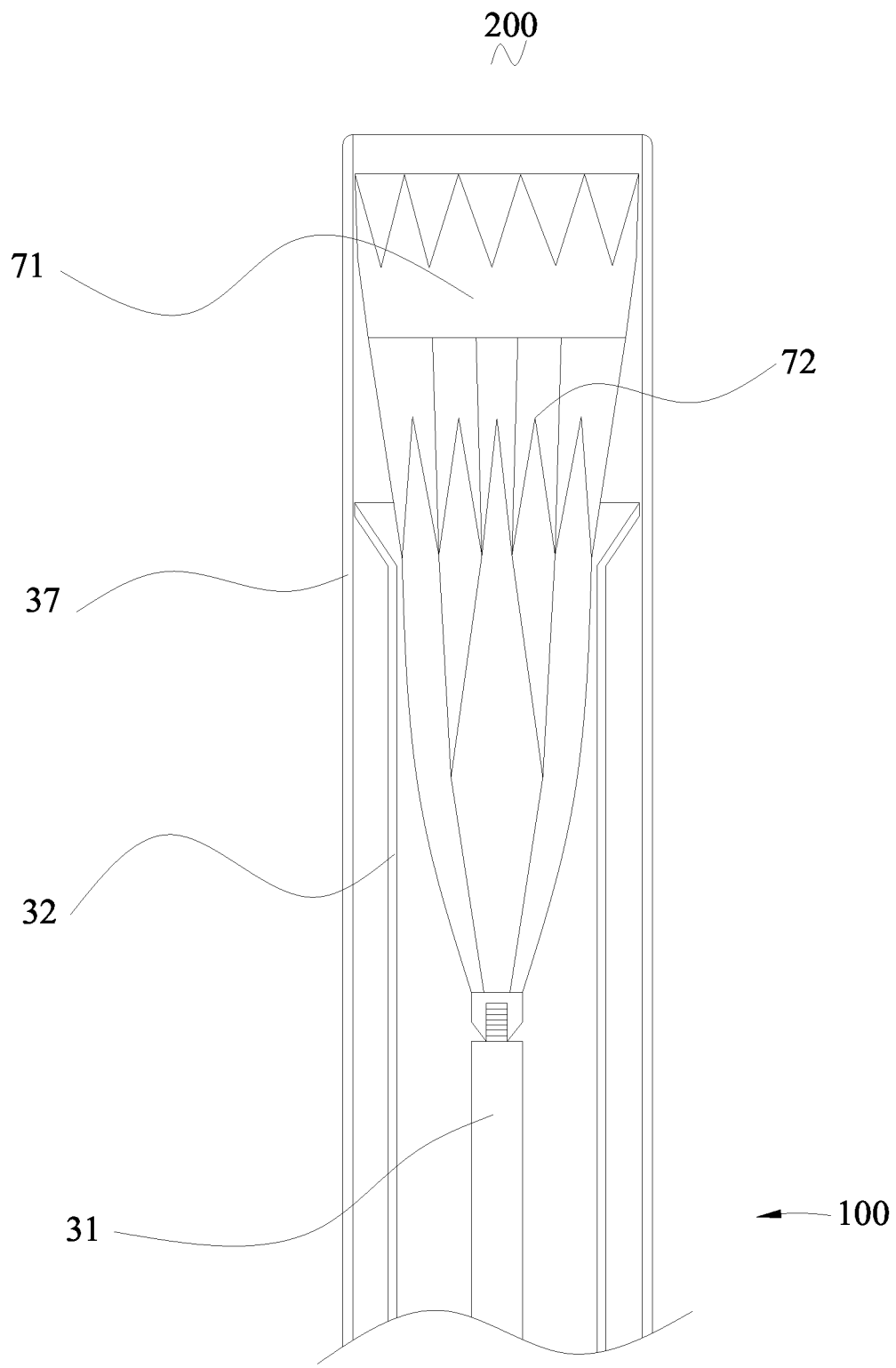
FIG. 8B is a diagram of a third state of cooperation between a conveyor and a valve prosthesis according to one embodiment.

As shown in FIG. 8B, the outer sheath 37 is then driven to slide in the direction from its proximal end to its distal end, and the valve prosthesis 71 is progressively received into the inner cavity of the outer sheath 37. The valve prosthesis 71 being fully received is a third state of the conveyor system 200. When the outer sheath 37 is driven to receive the valve prosthesis 71, the radial size of the valve prosthesis 71 is reduced due to the compression of the recovery sheath 32 to the valve stent 72, thereby greatly reducing the counter-reacting force of the valve prosthesis 71 to the outer sheath 37 (the counter-reacting force drives the outer sheath 37 to slide in the direction from its distal end to its proximal end). The convenience of making the valve prosthesis 71 received into the outer sheath 37 can be improved, and the difficulty of loading (via the outer sheath 37) the valve prosthesis 71 can be lowered. Meanwhile, deformation of the outer sheath 37 caused by the counter-reacting force of the valve prosthesis 71 to the outer sheath 37 is avoided, and destructive deformation of the valve stent 72 due to excessive frictional resistance between the outer sheath 37 and the valve prosthesis 71 is also avoided. The conveyor 100 allows the recovery process of the valve prosthesis 71 to be controllable by the self-locking mechanism 50.

It can be understood that the step of releasing the valve prosthesis 71 and the operation of receiving the valve prosthesis 71 are in a reverse order in the conveyor 100, but the convenience of releasing the valve prosthesis 71 is improved during the process of releasing the valve prosthesis 71 by the conveyor 100 via mutual cooperation between the recovery sheath 32 and the self-locking mechanism 50. Meanwhile, damage to the valve prosthesis 71 during release of the valve prosthesis 71 by the conveyor 100 can also be avoided.

Figure 9:
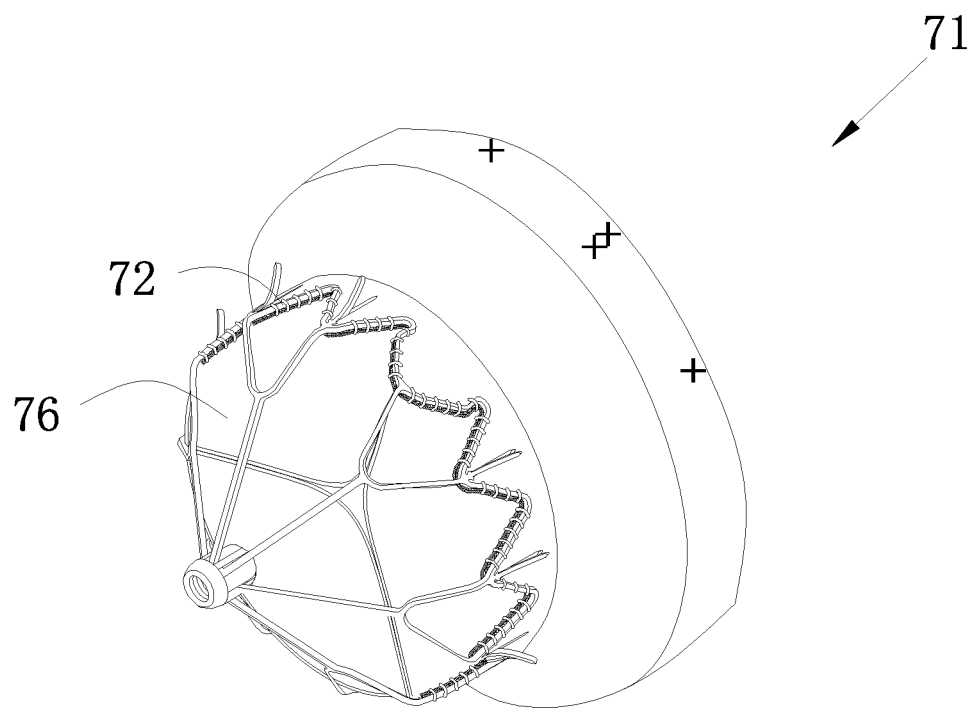
FIG. 9 is a schematic structural diagram of a heart valve according to one embodiment.

As shown in FIG. 9, the valve prosthesis 71 further includes leaflets 76 connected to the valve stent 72.

Figure 10:
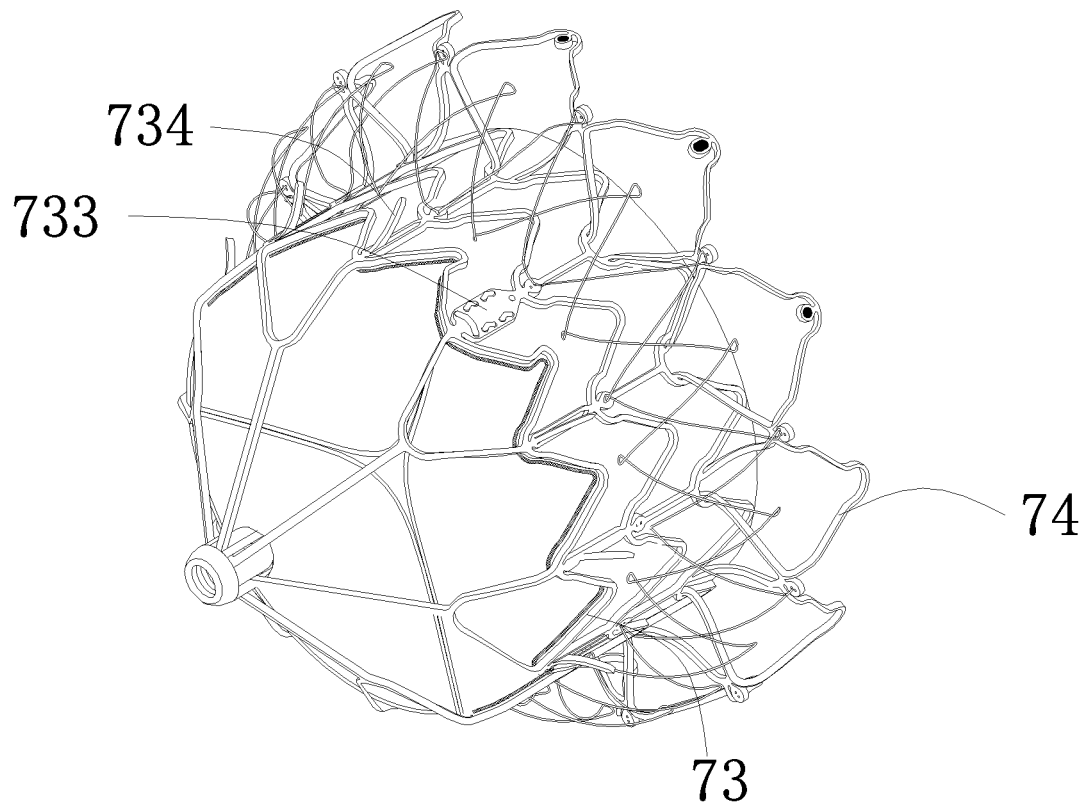
FIG. 10 is a schematic diagram of a partial structure of the heart valve shown in FIG. 9.

As shown in FIG. 9 and FIG. 10, the valve stent 72 includes a leaflet stent 73 and a skirt stent 74.

Figure 11:
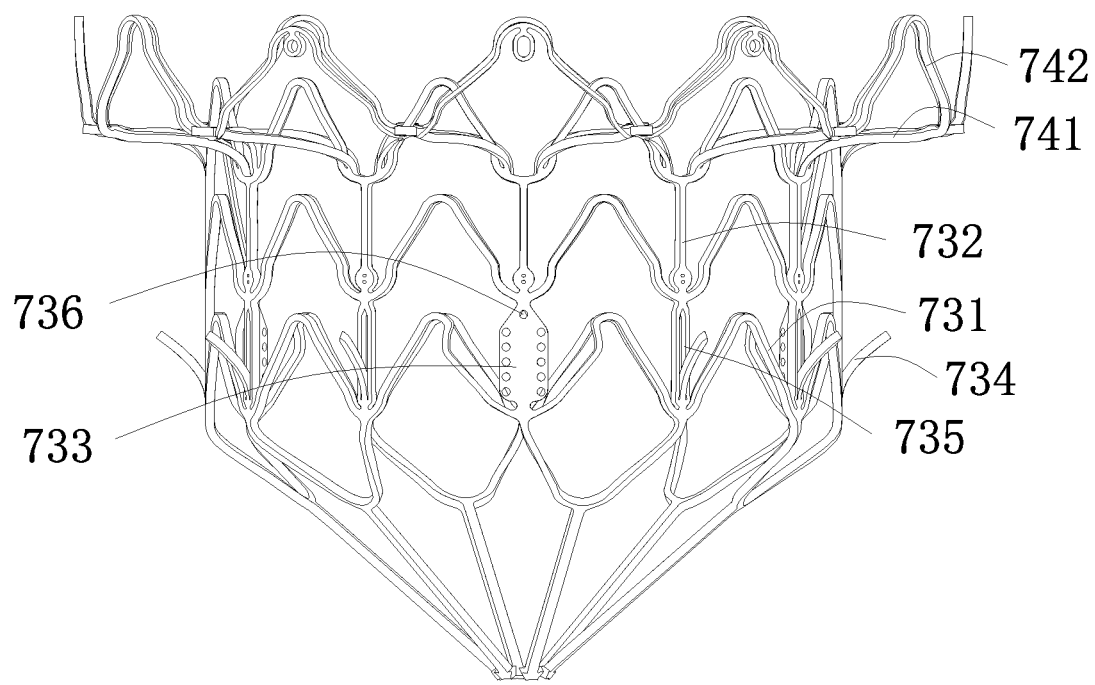
FIG. 11 is a schematic diagram of a partial structure of a valve stent of the heart valve of FIG. 9.

In the illustrated implementation mode, the leaflet stent 73 is generally cylindrical and has a first end and a second end opposite to the first end. It should be noted that in the illustrated implementation mode, the first end is a distal end (a blood inflow end) and the second end is a proximal end (a blood outflow end). The distal end denotes an end away from an operator in a surgical process, and the proximal end denotes an end close to the operator in the surgical process. As shown in FIG. 11, the leaflet stent 73 includes wave loops 731 and connection rods 732. The leaflet stent 73 includes a plurality of wave loops 731 spaced in the axial direction of the leaflet stent 73. The wave loops 731 provide a radial supporting force for the leaflet stent 73. In the illustrated implementation mode, the leaflet stent 73 includes three wave loops 731.

The three wave loops 731 are fixedly connected by a plurality of connection rods 732. In the illustrated implementation mode, the number of the connection rods 732 is the same as the number of troughs of the wave loops 731. One connection rod 732 is fixedly connected to the troughs of the three wave loops 731 at the same time. Of course, in other embodiments, the connection rods 732 may also be fixedly connected to other locations of the wave loops 731, such as peaks.

As shown in FIG. 11, connection pillars 733 fixed to the leaflets 76 are arranged on the connection rods 732, and the connection pillars 733 are located between two wave loops 731 close to the second end. The connection pillars 733 are provided with through holes. In the present embodiment, there are three connection pillars 733 uniformly distributed in a circumferential direction of the leaflet stent 73.

Figure 13:
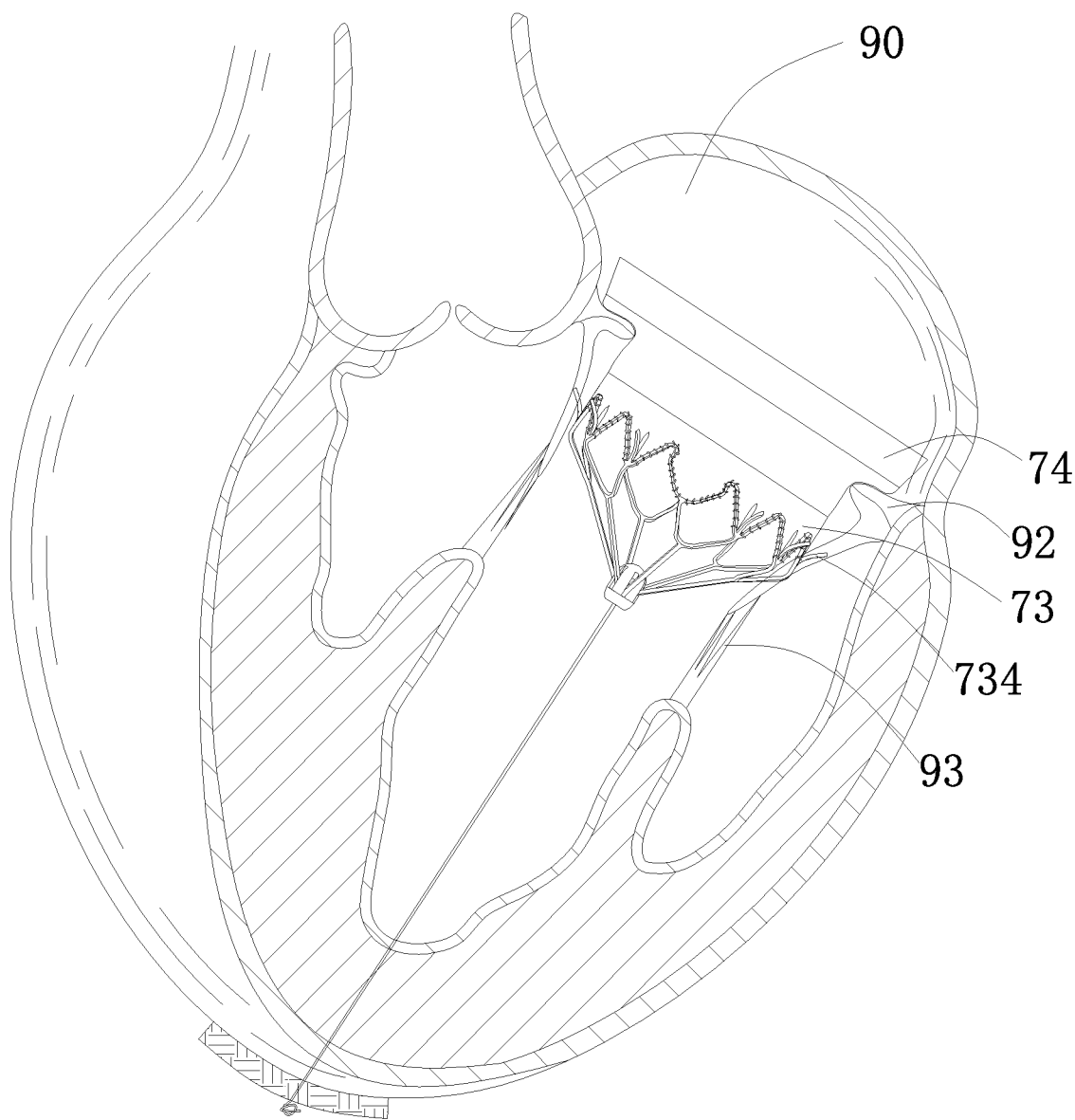
FIG. 13 is a schematic structural diagram of one state after the heart valve shown in FIG. 9 is implanted into the heart.

As shown in FIG. 10, the leaflet stent 73 is further provided with barbs 734. The barbs 734 extend to the outside from the radial direction of the leaflet stent 73, and an axial distance between ends, close to the leaflet stent 73, of the barbs 734 and an end, close to the leaflet stent 73, of the skirt stent 74 ranges from 5 mm to 16 mm. Preferably, the axial distance between the ends, close to the leaflet stent 73, of the barbs 734 and the end, close to the leaflet stent 73, of the skirt stent 74 ranges from 10 mm to 16 mm. As shown in FIG. 13, after the valve prosthesis 71 is implanted into the human heart 90, the human mitral valve leaflet would be squeezed by the leaflet stent 73 to the ventricular wall side and to maintain an opened state. The skirt stent 74 of the valve prosthesis 71 can be clamped on the mitral annulus 92 to prevent the valve prosthesis 71 from falling into the left ventricle, and the barbs 734 arranged on the leaflet stent 73 can hook the lower edge of the human leaflet. Under a pulling force of the valve chordae tendineae 93, the axial freedom of the valve prosthesis 71 can be restrained to prevent the valve prosthesis 71 from moving to the left atrium, so that the probability of movement of a heart valve prosthesis after implantation is effectively reduced. Furthermore, the barbs 734 can be hung on the human leaflet instead of piercing into a ventricular tissue to prevent friction between the barbs 734 and the ventricular tissue from injuring a cardiac muscle tissue around the atrium, and to avoid the risk of piercing the ventricular wall. Meanwhile, the barbs 734 are hung on the human leaflet, so that the human leaflet can wrap an outer side of the outflow end of the valve prosthesis 71, thereby reducing the risk of perivalvular leakage. Of course, in other embodiments, the axial distance between the ends, close to the leaflet stent 73, of the barbs 734 and the end, close to the leaflet stent 73, of the skirt stent 74, can range from 5 mm to 10 mm. The barbs 734 can also be fixed by piercing the human mitral valve leaflet.

Specifically, the barbs 734 are arranged on the connection rods 732 of the leaflet stent 73. Since the connection rods 732 extend through the first end and the second end of the leaflet stent 73, the rigidity is higher. When the barbs 734 are stressed, the connection rods 732 can bear a force transmitted from roots of the barbs 734 to prevent a partial deformation of the leaflet stent 73 caused by a torque generated on the barbs 734.

The barbs 734 are cut. Cutting patterns of the barbs 734 are located at end portions, away from the first end, of the connection rods 732 of the leaflet stent 73, and the barbs 734 are broken off during shaping. Specifically, as shown in FIG. 11, the connection rods 732 are cut to form barb slots 735. The ends that are away from the second end of the barbs 734 are broken off out from the barb slots 735 towards the radial direction of the leaflet stent 73 during shaping. The barbs 734 are accommodated in the barb slots 735 when the valve prosthesis 71 is received in the sheath. Positions on the connection rods 732, which are flush with the ends, away from the second end, of the barb slots 735, are provided with developing points 736. In the conveying process, the developing points 736 may be caused to be flush with a developing structure at an end portion of the sheath. At this time, the skirt stent 74 has been completely released from the sheath, but the barbs 734 are still located in the sheath. In this state, the position of the valve prosthesis 71 in the heart 90 is adjusted to facilitate accurate positioning of the valve prosthesis 71 in the heart 90 and also prevent the barbs 734 from puncturing the heart tissue. In the present embodiment, the developing points 736 are arranged on the connection pillars 733.

Figure 12:
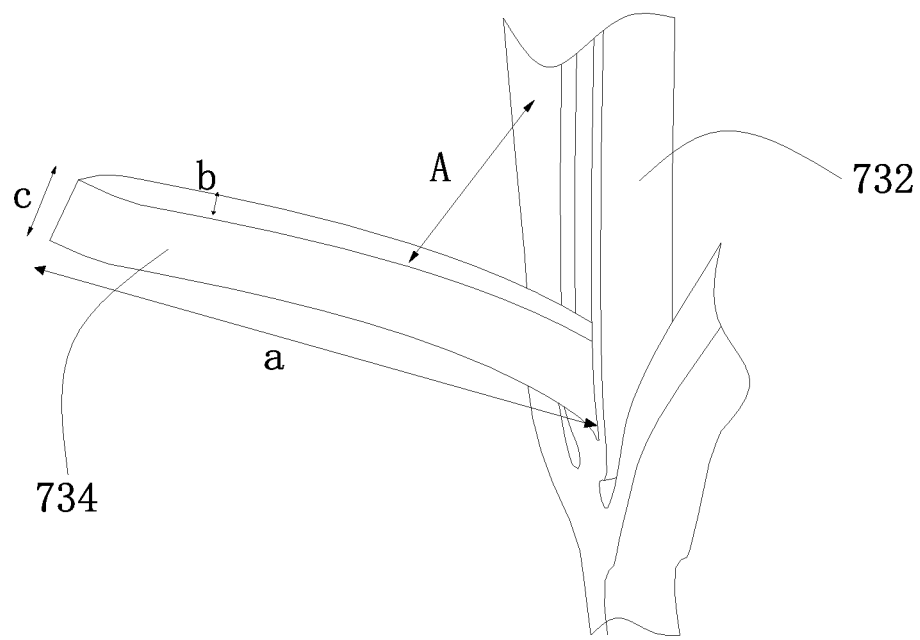
FIG. 12 is a schematic diagram of a partial structure of a valve stent of the heart valve of FIG. 9.

As shown in FIG. 12, the barbs 734 have a length a of 2 mm to 3 mm, or 3 mm to 5 mm, or 5 mm to 10 mm. In the present application, the length a of the barbs 734 refers to a length of a connection line between the end points of the ends, connected to the leaflet stent 73, of the barbs 734 and the end points of the ends, away from the leaflet stent 73, of the barbs 734. Preferably, the length a of the barbs 734 is 3 mm to 5 mm, so that the barbs 734 are not easily dislodged being hung on the human leaflet, and so as to make it difficult for the barbs 734 to pierce a tissue to form a perforated hole, or damage the tissue or a blood vessel. An included angle A between the barbs 734 and the leaflet stent 73 is 20 to 45 degrees, or 45 to 60 degrees, or 60 to 70 degrees. Preferably, the included angle A between the barbs 734 and the leaflet stent 73 is 45 to 60 degrees, so that the barbs 734 can be hung on the human leaflet more easily without significantly affecting a sheathing force. The barbs 734 have a width of 0.2 to 1.0 mm. Preferably, the barbs 734 have a width b of 0.2 to 0.4 mm, so that the sheathing force of the heart valve is not affected, and an effective axial supporting force can also be provided. In the present embodiment, the barbs 734 are of an equal-width (ends not considered) design, and the width of the barbs 734 in the present application is a width of a location other than the end. The thickness c of the barbs 734 is the same as the entire thickness of the leaflet stent 73, and is 0.2 to 0.6 mm. Preferably, the thickness c is 0.3 to 0.5 mm, which can guarantee the strength of the barbs 734 and can also provide a relatively high axial supporting force. A ratio of the width b to the thickness c of the barbs 734 ranges from 0.6 to 1, or from 1 to 1.2, or from 1.2 to 1.5, so that the strain of the barbs 734 when bearing a blood pressure load is relatively small, and the strength and fatigue resistance of the barbs 734 are improved. Preferably, the ratio of the width b to the thickness c of the barbs 734 ranges from 0.6 to 1, and the strength and fatigue resistance of the barbs 734 are relatively good.

As shown in FIG. 11, the skirt stent 74 includes supporting portions 741 and upwarp portions 742. The supporting portions 741 extend from the leaflet stent 73 in the radial direction of the leaflet stent 73, and the upwarp portions 742 extend, in a bending manner, from ends that are away from the leaflet stent 73 of the supporting portions 741 to the first end of the leaflet stent 73. The supporting portions 741 are used for fixing the valve prosthesis 71 to the mitral annulus 92 of the heart 90, and the upwarp portions 742 are used for preventing abrasion of an edge of the skirt stent 74 to tissues of the left atrium. In the case where there is no upwarp portion 742, the edges of the distal ends of the radial supporting portions 741 would be in direct contact with the atrial tissues, and a cutting effect would be formed on the atrial tissues under long-term heart beat, and cause damage to the atrial tissues. With the provision of the upwarp portions 742, the skirt stent 74 is in surface contact with the atrial tissues, thereby enlarging the contact area, reducing the contact pressure intensity, and avoiding the cutting effect formed by the skirt stent 74 on the heart tissues and the resulting abrasion caused by it.

The various technical features of the above-described embodiments may be combined in any manner. In order to simplify the description, all possible combinations of the various technical features in the above-described embodiments are not described. However, the combinations of these technical features should be deemed as falling within the scope in this specification, as long as they are not contradictory.

The embodiments set forth above represent only a few implementations of the present invention, and are described in more details more specifically, but are not to be construed as limiting the patent scope of the present invention. It should be noted that those of ordinary skill in the art can also make several modifications and improvements without departing from the concept of the present invention, and these modifications and improvements all fall within the protection scope of the present invention. Therefore, the protection scope of the patent of the present invention shall be subject to the claims attached.

The invention claimed is:

1. A conveyor system, comprising a valve prosthesis and a conveyor for conveying the valve prosthesis, the valve prosthesis comprises a valve stent; wherein the conveyor comprises a lumen assembly and a self-locking mechanism connected to the lumen assembly, the lumen assembly comprises an inner core tube, a recovery sheath movably sleeved outside the inner core tube, and an outer sheath movably sleeved outside the recovery sheath;

wherein the valve stent is radially compressed inside the distal end of the structure of a proximal end of the valve stent is received into an inner cavity of the recovery sheath, the valve stent is radially compressed inside the distal end of the outer sheath, and the distal end of the outer sheath receives the valve prosthesis in the inner cavity of the outer sheath, the self-locking mechanism is connected to the recovery sheath; and the outer sheath is movable relative to the inner core tube in an axial direction of the conveyor; the self-locking mechanism has a self-locked state and an unlocked state, when the self-locking mechanism is in the unlocked state, the recovery sheath is movable relative to the inner core tube in the axial direction of the conveyor; and when the self-locking mechanism is in the self-locked state, the recovery sheath stays stationary relative to the inner core tube.

2. The conveyor system according to claim 1, wherein the conveyor further comprises a housing assembly; an accommodating slot is defined in the housing assembly; the lumen assembly and the self-locking mechanism are mounted in the accommodating slot; a rack track is arranged on an inner side wall of the housing assembly; the self-locking mechanism comprises a limiting member connected to the recovery sheath; the limiting member comprises a main body and limiting teeth arranged on the main body; the limiting teeth cooperate with the rack track; the limiting member movably cooperates with the recovery sheath in a radial direction of the recovery sheath, when the limiting teeth follow the limiting member to move in the radial direction of the recovery sheath to mesh with the rack track, the self-locking mechanism is switched to the self-locked state; and after the limiting teeth follow the limiting member to move in the radial direction of the recovery sheath to be separated from the rack track, the self-locking mechanism is switched to the unlocked state.

3. The conveyor system according to claim 2, wherein the recovery sheath comprises a recovery sheath body and a sheath joint fixed at a proximal end of the recovery sheath body, and a groove or a bulge is arranged on the sheath joint, when a groove is defined in the sheath joint, a bulge aligned with the groove is on the main body; when a bulge is arranged on the sheath joint, a groove is aligned with the bulge is defined in the main body; the bulge movably cooperates with the groove; and the limiting member movably cooperates with the recovery sheath through the bulge.

4. The conveyor system according to claim 3, wherein a tooth height of the rack track is equal to a tooth height of the limiting teeth; a protruding length of the bulge is greater than or equal to the tooth height of the rack track; and a depth of the groove is greater than or equal to the tooth height of the rack track.

5. The conveyor system according to claim 3, wherein the recovery sheath further comprises a necking structure; the necking structure is fixed at a distal end of the recovery sheath body; an inner diameter of the necking structure is gradually reduced in a direction from the distal end to the proximal end; an inner diameter of the proximal end of the necking structure is equal to an inner diameter of the distal end of the recovery sheath body; and the maximum outer diameter of the necking structure is less than or equal to an inner diameter of the outer sheath.

6. The conveyor system according to claim 2, wherein a central axis of the recovery sheath is aligned with a central axis of the housing assembly; two rack tracks are provided; the two rack tracks are symmetrically distributed in a diameter direction of the recovery sheath; two limiting members are provided; the limiting members are in one-to-one correspondence with the rack tracks;

the self-locking mechanism further comprises elastic members compressed between the two limiting members; a force application direction of an elastic force generated by the elastic members is perpendicular to the central axis of the housing assembly; and the elastic force generated by the elastic members drives the limiting teeth of the two limiting members to move to mesh with the rack tracks.

7. The conveyor system according to claim 6, wherein the elastic members are arranged in pairs; the paired elastic members are respectively located on two sides of the recovery sheath; and two adjacent pairs of elastic members are arranged to extend along an axial line of the recovery sheath.

8. The conveyor system according to claim 2, wherein a track hole extending in an axial direction of the housing assembly is also defined in the housing assembly; the track hole and the accommodating slot extend through each other; an extending direction of the track hole is the same as an extending direction of the rack track; the track hole is defined in the rack track; the limiting member further comprises a connection portion fixedly connected to the main body; the connection portion extends out of the track hole from the accommodating slot; and the connection portion movably cooperates with the track hole.

9. The conveyor system according to claim 8, wherein the limiting member further comprises a button, and the button is fixedly connected to the connection portion.

10. The conveyor system according to claim 1, wherein the valve prosthesis is detachably connected to the lumen assembly of the conveyor.

\* \* \* \* \*